(12) United States Patent
Schaack et al.

(10) Patent No.: US 10,562,009 B2
(45) Date of Patent: Feb. 18, 2020

(54) METHOD FOR PRODUCING RUTHENIUM/IRON/CARBON CARRIER CATALYSTS

(71) Applicant: BASF SE, Ludwigshafen am Rhein (DE)

(72) Inventors: Bernd Bastian Schaack, Bensheim (DE); Helmut Wanisch, Hassloch (DE); Barbara Wucher, Laudenbach (DE); Sabine Huber, Bobenheim-Roxheim (DE)

(73) Assignee: BASF SE, Ludwigshafen am Rhein (DE)

( * ) Notice: Subject to any disclaimer, the term of this patent is extended or adjusted under 35 U.S.C. 154(b) by 20 days.

(21) Appl. No.: 15/765,821

(22) PCT Filed: Oct. 4, 2016

(86) PCT No.: PCT/EP2016/073678
§ 371 (c)(1),
(2) Date: Apr. 4, 2018

(87) PCT Pub. No.: WO2017/060243
PCT Pub. Date: Apr. 13, 2017

(65) Prior Publication Data
US 2018/0297013 A1 Oct. 18, 2018

(30) Foreign Application Priority Data
Oct. 5, 2015 (EP) .................... 15188361

(51) Int. Cl.
*B01J 37/03* (2006.01)
*B01J 21/18* (2006.01)
(Continued)

(52) U.S. Cl.
CPC ........... *B01J 21/18* (2013.01); *B01J 23/8906* (2013.01); *B01J 33/00* (2013.01); *B01J 37/0018* (2013.01);
(Continued)

(58) Field of Classification Search
CPC ........ B01J 21/18; B01J 23/8906; B01J 33/00; B01J 37/0018; B01J 37/03; B01J 37/035;
(Continued)

(56) References Cited

U.S. PATENT DOCUMENTS 4,465,787 A 8/1984 Horner et al.
5,118,884 A * 6/1992 Didillon ................ C07C 29/141
502/242

(Continued)

FOREIGN PATENT DOCUMENTS

EP 0071787 A2 2/1983
EP 0947493 A1 10/1999
(Continued)

OTHER PUBLICATIONS

International Search Report for PCT/EP2016/073678 dated Nov. 10, 2016.
Written Opinion of the International Searching Authority for PCT/EP2016/073678 dated Nov. 10, 2016.

*Primary Examiner* — Patricia L. Hailey
(74) *Attorney, Agent, or Firm* — Drinker Biddle & Reath LLP

(57) ABSTRACT

The present invention relates to a process for producing iron-doped ruthenium-carbon support catalysts and also their use for the selective liquid-phase hydrogenation of carbonyl compounds to the corresponding alcohols, in particular for the hydrogenation of citral to geraniol or nerol or of citronellal to citronellal.

17 Claims, 2 Drawing Sheets

(51) Int. Cl.
*B01J 23/89* (2006.01)
*B01J 33/00* (2006.01)
*C07C 29/141* (2006.01)
*B01J 37/00* (2006.01)
*B01J 37/18* (2006.01)
*C07C 33/025* (2006.01)

(52) U.S. Cl.
CPC ............. *B01J 37/035* (2013.01); *B01J 37/18* (2013.01); *C07C 29/141* (2013.01); *C07C 33/025* (2013.01); *B01J 2523/821* (2013.01); *B01J 2523/842* (2013.01)

(58) Field of Classification Search
CPC .......................... B01J 37/18; B01J 2523/821; B01J 2523/842; C07C 29/141; C07C 33/025
USPC .......................... 502/185, 326; 568/874, 883
See application file for complete search history.

(56) References Cited

U.S. PATENT DOCUMENTS

| | | |
|---|---|---|
| 5,939,589 A | 8/1999 | Kaibel et al. |
| 6,150,564 A | 11/2000 | Bröcker et al. |
| 6,743,956 B1 * | 6/2004 | Haake ................... C07C 29/141 |
| | | 564/422 |
| 7,101,824 B2 | 9/2006 | Gerlach et al. |
| 7,560,496 B2 | 7/2009 | Kuhrs et al. |
| 8,742,174 B2 | 6/2014 | Mägerlein et al. |

FOREIGN PATENT DOCUMENTS

| | | |
|---|---|---|
| EP | 1317959 A1 | 6/2003 |
| WO | WO-2006077236 A1 | 7/2006 |
| WO | WO-2011082967 A1 | 7/2011 |

* cited by examiner

METHOD FOR PRODUCING RUTHENIUM/IRON/CARBON CARRIER CATALYSTS

CROSS-REFERENCE TO RELATED APPLICATIONS

This application is a national stage application (under 35 U.S.C. § 371) of PCT/EP2016/073678, filed Oct. 4, 2016, which claims benefit of European Application No. 15188361.8, filed Oct. 5, 2015, both of which are incorporated herein by reference in their entirety.

All documents cited in the present patent application are incorporated by reference in their entirety into the present disclosure.

The present invention relates to a process for producing iron-doped ruthenium-carbon support catalysts and also their use for the selective liquid-phase hydrogenation of carbonyl compounds to the corresponding alcohols, in particular for the hydrogenation of citral to geraniol or nerol or of citronellal to citronellol.

PRIOR ART

Various processes for producing catalysts are known from the prior art. The processes differ essentially in terms of the precursors of the active components used or in the manner of the deposition/treatment of the active components on the carbon support.

EP 0 071 787 discloses ruthenium-iron-carbon hydrogenation catalysts and also the production and use thereof for the selective hydrogenation of unsaturated carbonyl compounds. The Ru—Fe-carbon catalyst used is produced by impregnation of activated carbon powder with ruthenium chloride solution, drying and subsequent mixing with iron oxide. The catalyst is reduced by means of hydrogen at 500° C.

However, the use of chlorides presents technical problems since chloride is highly corrosive. Thus, impregnation and drying of the active components have to be carried out in expensive, corrosion-resistant apparatuses. The reduction forms HCl which can damage the reduction furnace and chloride can remain on the catalyst and lead to corrosion in the production reactor when the catalyst is used in the hydrogenation.

If the nitrate salts of ruthenium are used instead of the chlorides, this can lead to safety problems since nitrate/carbon mixtures can be explosive. A further disadvantage of the process described is the sequential doping with $Fe_2O_3$, which requires an additional process step.

Various hydrogenation processes for alpha,beta-unsaturated carbonyl compounds are likewise known from the prior art. However, it is difficult to obtain high selectivities of the corresponding alcohols when using the processes described and the catalysts employed. For example, in the hydrogenation of citral, it is possible that not only the aldehyde group but also the olefinic double bonds or only the double bond conjugated with the aldehyde group are/is hydrogenated, so that by-products such as citronellol or citronellal can be formed in addition to the unsaturated alcohols geraniol and nerol.

EP 1 317 959 discloses a process for producing ruthenium-iron-carbon support catalysts in which the catalyst is reduced in a stream of hydrogen at from 400 to 600° C. Good results are achieved using this process or the catalysts produced in this way.

Both for economic and ecological reasons, it is desirable to improve the catalysts and the production processes for them even further in order to obtain a further improvement in the environmental compatibility and economics. This is an important aspect especially for industrial applications.

OBJECT

It was an object of the present invention to develop a further-improved process for producing a ruthenium-iron-carbon support catalyst, in particular for the selective hydrogenation of olefinically unsaturated carbonyl compounds to the correspondingly unsaturated alcohols, without the above-described disadvantages and with even better results.

The catalyst should have an even better catalyst activity and long-term stability and also, in particular, in the hydrogenation of citral to geraniol/nerol lead to high citral conversions and at the same time low selectivities to citronellol.

Furthermore, the possible achievement of complete conversion of citral by means of the catalyst should be more critical than selectivity in respect of the products of the hydrogenation to geraniol and nerol.

The use of corrosive starting materials such as chloride salts or explosive intermediates such as nitrate-impregnated carbons should be avoided in the production of the catalyst.

In particular, improved catalysts should be produced by more economical processes. In addition, the use of the catalysts in the reduction of carbonyl compounds should make more economical processes, in particular in respect of the energy consumption, possible.

The catalysts should, in particular, have increased activities and improved long-term stabilities in liquid-phase hydrogenations of carbonyl compounds.

ACHIEVEMENT OF THE OBJECT

The object was achieved according to the invention by a process for producing a ruthenium-carbon support catalyst comprising from 0.1 to 5% by weight of iron in addition to from 0.1 to 10% by weight of ruthenium on a carbon support by
a) introduction of the support into water
b) simultaneous addition of the catalytically active components in the form of solutions of their metal salts
c) coprecipitation of the catalytically active components on the support by addition of a base
d) separation of the catalyst from the aqueous phase of the support suspension
e) drying of the catalyst
f) reduction of the catalyst in a stream of hydrogen at less than 400° C., preferably from 120 to 300° C., particularly preferably from 150 to 250° C., in particular from 180 to 220° C.
g) removal of the catalyst from the reduction reactor under relatively nonflammable liquids
   or
   passivation of the catalyst by passing a diluted oxygen stream over it
   or
   passivation of the catalyst by passing a diluted oxygen stream over it and removal
   of the catalyst from the reduction reactor under relatively nonflammable liquids; catalysts produced by means of this process and also the use thereof in and processes for the selective liquid-phase hydrogenation of carbonyl compounds.

Definitions of Terms

In the context of the present invention, all amounts indicated are on a weight basis, unless indicated otherwise.

For the purposes of the present invention, the term "room temperature" means a temperature of 20° C. Temperatures indicated are in degrees Celsius (° C.), unless indicated otherwise.

Unless indicated otherwise, the reactions and process steps referred to are carried out at atmospheric pressure, i.e. at 1013 mbar.

For the purposes of the present invention, the formulation "and/or" encompasses both any particular element and all combinations of the elements mentioned in the respective list.

"Oxidation" means increasing the oxidation number of an atom/element, preferably by loss of electrons.

DETAILED DESCRIPTION

The present invention firstly provides a process for producing a ruthenium-carbon support catalyst comprising from 0.1 to 5% by weight of iron in addition to from 0.1 to 10% by weight of ruthenium on a carbon support by
a) introduction of the support into water
b) simultaneous addition of the catalytically active components in the form of solutions of their metal salts
c) coprecipitation of the catalytically active components on the support by addition of a base
d) separation of the catalyst from the aqueous phase of the support suspension
e) drying of the catalyst
f) reduction of the catalyst in a stream of hydrogen at from 100 to less than 400° C., preferably from 120 to 300° C., particularly preferably from 150 to 250° C., in particular from 180 to 220° C.
g) removal of the catalyst from the reduction reactor under relatively nonflammable liquids
or
passivation of the catalyst by passing a diluted oxygen stream over it
or
passivation of the catalyst by passing a diluted oxygen stream over it and removal of the catalyst from the reduction reactor under relatively nonflammable liquids.

In one variant of the present invention, step f) is carried out at from 190 to 210° C., in particular at 200° C.

The steps (b) and (c) in the process of the invention can be carried out either successively or simultaneously.

The invention further provides for the use of the ruthenium-iron-carbon support catalysts produced by the process of the invention for the selective liquid-phase hydrogenation of carbonyl compounds of the general formula I,

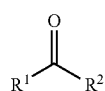

(I)

where
$R^1$, $R^2$ can each be, independently of one another, identical or different and are each hydrogen or a saturated or a monounsaturated or polyunsaturated straight-chain or branched, optionally substituted, $C_1$-$C_{20}$-alkyl radical, an optionally substituted aryl radical or an optionally substituted heterocyclic group,
to the corresponding alcohols of the general formula II

(II)

where $R^1$, $R^2$ are as defined above.

As carbonyl compounds, it is possible to use both saturated and olefinically unsaturated carbonyl compounds.

For the purposes of the present invention, a saturated or monounsaturated or polyunsaturated straight-chain or branched $C_1$-$C_{20}$-alkyl radical is, unless indicated otherwise, a methyl, ethyl, propyl, isopropyl, n-butyl, i-butyl, t-butyl, pentyl, hexyl, heptenyl, octyl, nonyl, decyl, 1-propenyl, 2-propenyl, 2-methyl-2-propenyl, 1-pentenyl, 1-methyl-2-pentenyl, isopropenyl, 1-butenyl, hexenyl, heptenyl, octenyl, nonenyl or a decenyl radical or the radicals corresponding to the compounds employed as indicated further below.

For the purposes of the present invention, an aryl radical is a benzyl, phenyl or naphthyl radical.

For the purposes of the present invention, a heterocyclic group is, for example, a pyridine, pyrimidine, pyridazine, pyrazine, piperazine, imidazole, furan, oxazole, isothiazole, isoxazole, 1,2,3-triazole or 1,2,4-triazole, thiazole, thiophene or indole ring.

Substituents can be methyl, ethyl, propyl, i-propyl, butyl, t-butyl, fluorine, chlorine, bromine, iodine, nitro or amino radicals.

As saturated carbonyl compounds, use is made of, for example, 3,7-dimethyloctan-1-al and isomers thereof, tetrahydrogeranyl acetone, hexahydrofarnesylacetone, 6-methylheptanone or isovaleraldehyde.

As olefinically unsaturated carbonyl compounds, it is possible to use, for example, citronellal, H-geranylacetone, H-nerolidol, methyl vinyl ketone, mesityl oxide, pseudoionene, dihydrofarnesylacetone, lysmeral, methylhexenone, particularly preferably citronellal, or else alpha,beta-unsaturated carbonyl compounds, for example acrolein, methacrolein, crotonaldehyde, prenal, farnesal or citral, particularly preferably citral.

The relatively nonflammable liquids mentioned under step g) of the process of the invention are liquids having a flashpoint of greater than 80° C., preferably greater than 100° C., for example water, geraniol, pentanediol, ethylene glycol or nerol or mixtures thereof, particularly preferably geraniol or nerol or mixtures thereof.

In one variant of the present invention, water is used as relatively nonflammable liquid in step g).

The simultaneous precipitation of the metal salts of the active components ruthenium and iron surprisingly leads to improved catalyst activity, selectivity and operating life. The precipitation of the metals in the form of their hydroxides avoids the problems of corrosion and explosion risk indicated in the prior art.

As metal salts of the active components ruthenium and iron, it is possible to use the chlorides, nitrates, nitrosyl nitrates, acetates, oxides, hydroxides, acetylacetonates, preferably the chlorides and nitrates.

The catalyst can be produced either as fixed-bed catalyst or suspended catalyst by means of the process of the invention.

For the purposes of the present invention, the carbon support materials are, for example, graphites, carbon blacks or activated carbon, but preferably activated carbon, e.g. NORIT SX Plus®. Depending on whether the catalyst is to be produced as suspended catalyst or fixed-bed catalyst, the carbon support material is used in pulverulent form or in the form of extrudates, spheres, crushed material, etc. The carbon support can be pretreated, for instance by oxidation by means of nitric acid, oxygen, hydrogen peroxide, hydrochloric acid, etc., before being doped.

In detail, the production of the catalyst according to the invention is carried out as follows:

To produce a suspended catalyst, the carbon support is suspended in water (step a)) and the resulting support suspension is used either without further pretreatment, i.e. without setting of a particular pH, or with setting of a pH of less than 6 by means of an acid, for example $HNO_3$, or of greater than 8 by means of a base, for example NaOH, for the further process.

In step b), the active components ruthenium and iron are added simultaneously in the form of solutions of their metal salts. The addition is preferably carried out at an elevated temperature of the suspension, particularly preferably at a temperature in the range from 50 to 95° C., particularly preferably at a temperature of from 70 to 90° C. Subsequently, to precipitate the catalytically active components on the support, a base, for example $Na_2CO_3$, $NaHCO_3$, $(NH_4)_2CO_3$, $NH_3$, urea, NaOH, KOH or LiOH, preferably NaOH, is slowly added and the pH is increased to a value in the range from 6 to 14, preferably to from 8 to 12, particularly preferably to 9 (step c)). The addition of the base is preferably carried out at elevated temperature, particularly preferably at a temperature in the range from 50 to 95° C., preferably at a temperature of from 70 to 90° C. The addition of the base can also be carried out simultaneously with the addition of the metal salt solution, for instance in order to keep the pH of the suspension constant, preferably at a pH of from 8 to 14, particularly preferably 9. Since ruthenium and iron are mainly present as hydroxides after the precipitation, chloride or nitrate anions are washed out to an unproblematically low content in the washing and separation of the catalyst from the aqueous phase (step d)) following the precipitation.

The filter cake is subsequently dried (e)) under reduced pressure or inert gas and the catalyst is then reduced (f)) in a stream of hydrogen, possibly diluted with an inert gas such as nitrogen, at less than 100° C., mostly at from 100 to less than 400° C., preferably from 120 to 300° C., particularly preferably from 150 to 250° C., in particular from 180 to 220° C. The hydrogen content of the hydrogen stream is in the range from 5 to 100% by volume, preferably from 5 to 50% by volume; in one variant, the content can be 10% by volume.

Finally, the catalyst is then cooled to temperatures below 40° C. and subsequently removed from the reduction reactor under, for example, water or a relatively nonflammable liquid (g)).

Instead of this removal from the reduction reactor or in addition thereto, passivation can be carried out.

In a variant of the present invention, the passivation is carried out by passing a diluted oxygen stream over it (g)).

In a variant of the present invention, the passivation is carried out at room temperature by firstly passing pure nitrogen over it and then slowly, for example over a period of one hour, replacing the nitrogen by air until pure air is being passed over the catalyst.

As diluted oxygen stream, it is in principle possible to use any gas stream comprising oxygen in an amount which does not predominate (i.e. less than 50% by volume). Examples are inert gas/oxygen mixtures having an oxygen content of <50% by volume.

As inert gases, mention may be made of, in particular, nitrogen, helium, neon, argon, $CO_2$, with nitrogen being particularly advantageous.

Mixtures in which proportions of less than 10% by volume, preferably less than 5% by volume, of oxygen are present, in particular mixtures of 1% by volume of oxygen in an inert gas, are particularly advantageous; in preferred embodiments, the inert gas is nitrogen.

It is likewise possible to use air as diluted oxygen stream, optionally diluted by additional nitrogen.

In a variant of the present invention, the reduction (f) is carried out at from 190 to 210° C., in particular 200° C.

The production of the fixed-bed catalysts is carried out in a manner analogous to the process described for the suspended catalyst, using extrudates, spheres, crushed material, etc., instead of the pulverulent support material in step (a). The characteristic lengths of these shaped bodies (diameter, length, etc.) are generally above 1 mm. When dispersing the extrudates in water, care has to be taken to ensure that the mechanical stresses thereof are kept as low as possible in order to minimize abrasion. The extrudates are advantageously washed with water in order to remove weakly adhering fine carbon particles before use in the synthesis of the catalyst.

The catalysts according to the invention generally comprise from 0.1 to 10% by weight of ruthenium on a carbon support, preferably on activated carbon.

The BET surface area of the catalysts is, corresponding to the carbon supports used for the production process, from about 100 to 1500 m$^2$/g, preferably from about 800 to 1200 m$^2$/g. The particle size of the ruthenium crystallites is mostly below 10 nm, determined by means of CO adsorption, and thus corresponds to the values known from the literature for ruthenium-carbon catalysts.

The values given for the % by weight of ruthenium and iron comprised in the catalyst are always based on the dry mass of the catalyst in the present patent application.

The particles of the suspended catalysts produced by means of the process of the invention have a density which is (mostly) equal to or less than the density of the mixture in which the hydrogenation is carried out since the particles for catalysis remain in suspension and do not sediment.

The catalyst produced according to the invention is of particular importance for the selective hydrogenation of carbonyl compounds, preferably for the selective hydrogenation of unsaturated carbonyl compounds, particularly preferably for the hydrogenation of citral to geraniol or nerol or of citronellal to citronellol.

The catalyst produced according to the invention hydrogenates the aldehyde group of the carbonyl compound with surprisingly high selectivity.

The hydrogenation process can be carried out either continuously or batchwise in suspension or in a fixed bed. The continuous mode of operation is particularly advantageous.

Conventional reactor concepts as are described, for example, in Ullmann's Encyclopedia of Industrial Chemistry, Sixth Edition, 2000 Electronic Release, are possible for the suspension variant or fixed-bed variant.

The continuous or batch suspension process can, for example, be carried out as described in EP 0 947 493 or U.S. Pat. No. 5,939,589. Both in the batch suspension mode of operation and in the continuous suspension mode of operation, the catalyst is used in finely divided form, with the particle size being less than 1 mm, preferably in the range from 1 to 100 μm, particularly preferably from 10 to 50 μm, in each case measured by means of laser light scattering. In a variant of the present invention, the particle size distribution has a d50 in the range from 15 to 25 μm. Suitable instruments for this purpose are, for example, the Mastersizer 2000 or the Mastersizer 3000, both from the Malvern company.

In the case of the fixed-bed variant, the catalyst is used in shapes customary for fixed-bed catalysts, for example in the form of extrudates, crushed material, pellets or spheres. Typical extrudate diameters are in the range from 1 to 5 mm, and the extrudate lengths are in the range from 1 to 20 mm. The reactor can be operated in the downflow mode or upflow mode.

The reaction is, both in the suspension mode or in the fixed-bed variant, carried out at atmospheric pressure or under a pressure of from 1 to 200 bar, preferably from 10 to 100 bar, particularly preferably from 20 to 50 bar. The temperatures are in the range from 25 to 200° C., preferably from 60 to 100° C. The reaction can be carried out either with or without solvents. As solvents, it is possible to use lower alcohols such as methanol, ethanol or isopropyl alcohol. Furthermore, an organic base such as trimethylamine can be added if required.

The hydrogenation of the carbonyl compound over the catalysts produced according to the invention is preferably carried out in the presence of a tertiary amine.

In principle, any tertiary amines are suitable, so that their chemical nature is of no importance, as long as they cannot react otherwise with the reaction partners as a result of their functional groups.

Possible amines are, for example, those mentioned in EP 0 071 787.

The amount of the amines can vary within a very wide range.

In one variant of the present invention, the amount of the amines is from 1 to 5% by weight of the amount of the carbonyl compound used.

The catalysts of the invention/produced according to the invention display increased long-term stability and activity compared to those described in EP 1 317 959.

Higher conversions are achieved more quickly when using the catalysts of the invention/produced according to the invention than when using the catalysts as described in EP 1 317 959 and the conversions on continued use are above those of EP 1 317 959 (cf. FIG. 3).

These results were surprising because reduction of the iron compound occurs at the reduction temperature of from 100 to less than 400° C., preferably from 120 to 300° C., particularly preferably from 150 to 250° C., in particular from 180 to 220° C. Although iron cannot be reduced at these temperatures, in particular at from 180 to 220° C., the combination with ruthenium nevertheless leads to reduction even at these temperatures; this was not known hitherto and higher temperatures were consequently employed in the prior art. The catalyst present in reduced form could be confirmed by X-ray photoelectron spectroscopy (XPS) and also temperature-programmed reduction (TPR).

Due to the increased activity and long-term stability of the catalysts of the invention/produced according to the invention, the capacities and running times of the production plants can be increased, which, particularly in the case of industrial plants, produces tremendous ecological and economic advantages.

A further advantage of the present invention is that, due to the lower reduction temperature, the reduced catalyst can be introduced directly into water even without passivation, which saves time and money and is thus a considerable process engineering advantage and ecological/economic advantage.

Furthermore, less catalyst is required for the same amount of product.

The various embodiments of the present invention, for example but not exclusively those of the various dependent claims, can be combined with one another in any desired way.

This figure shows catalyst recycling for a catalyst according to the invention, reduced at 200° C. (produced as per example 3).

Figure 1:
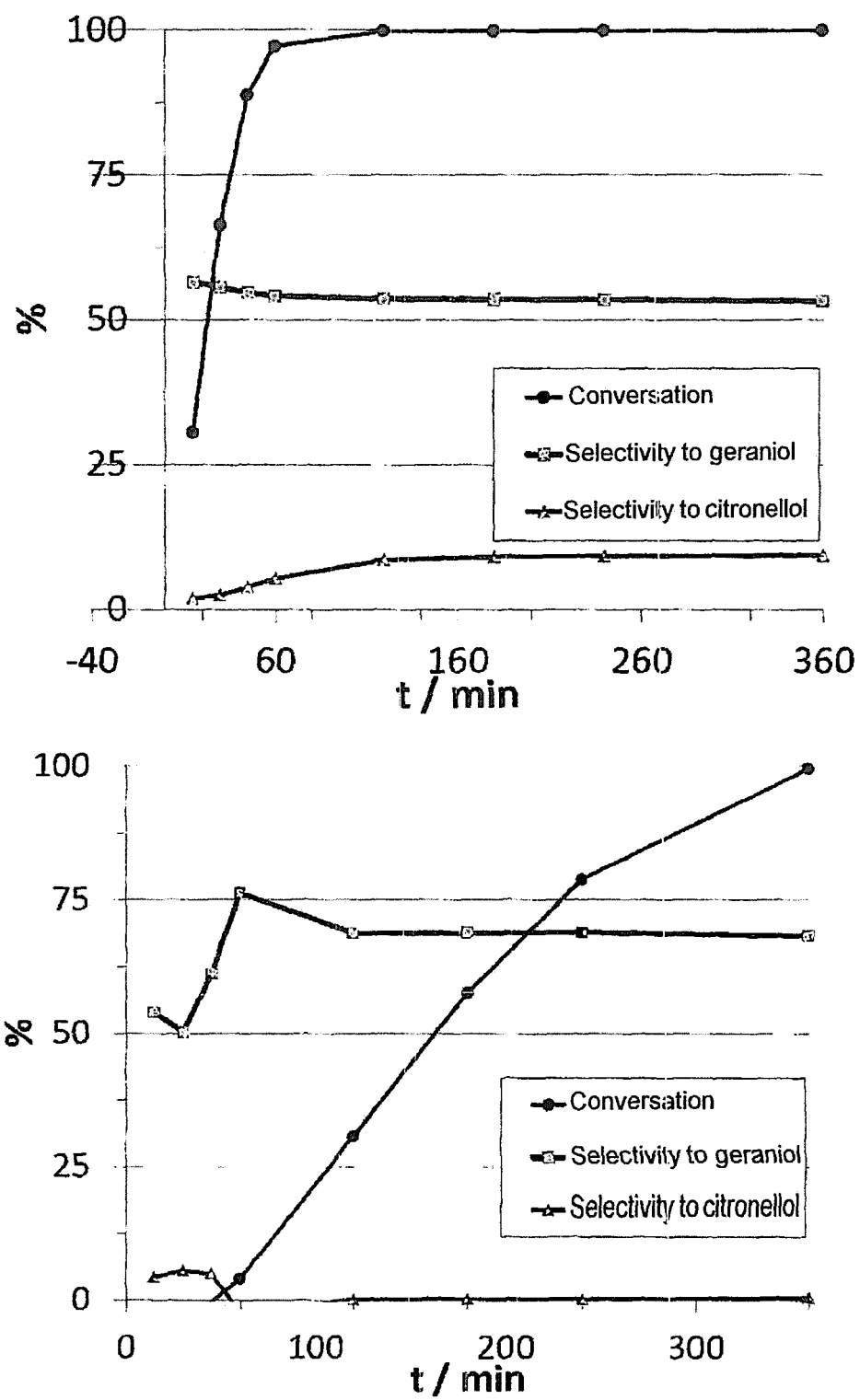
FIG. 1.

This catalyst is active enough to achieve complete conversion even in the fourth cycle after 360 minutes (FIG. 1, bottom). In the first cycle, complete conversion was achieved after 100 minutes (FIG. 1, top).

FIG. 2:

This figure shows catalyst recycling for a catalyst according to EP 1 317 959, reduced at 500° C. (produced as per comparative example 2).

Figure 2:
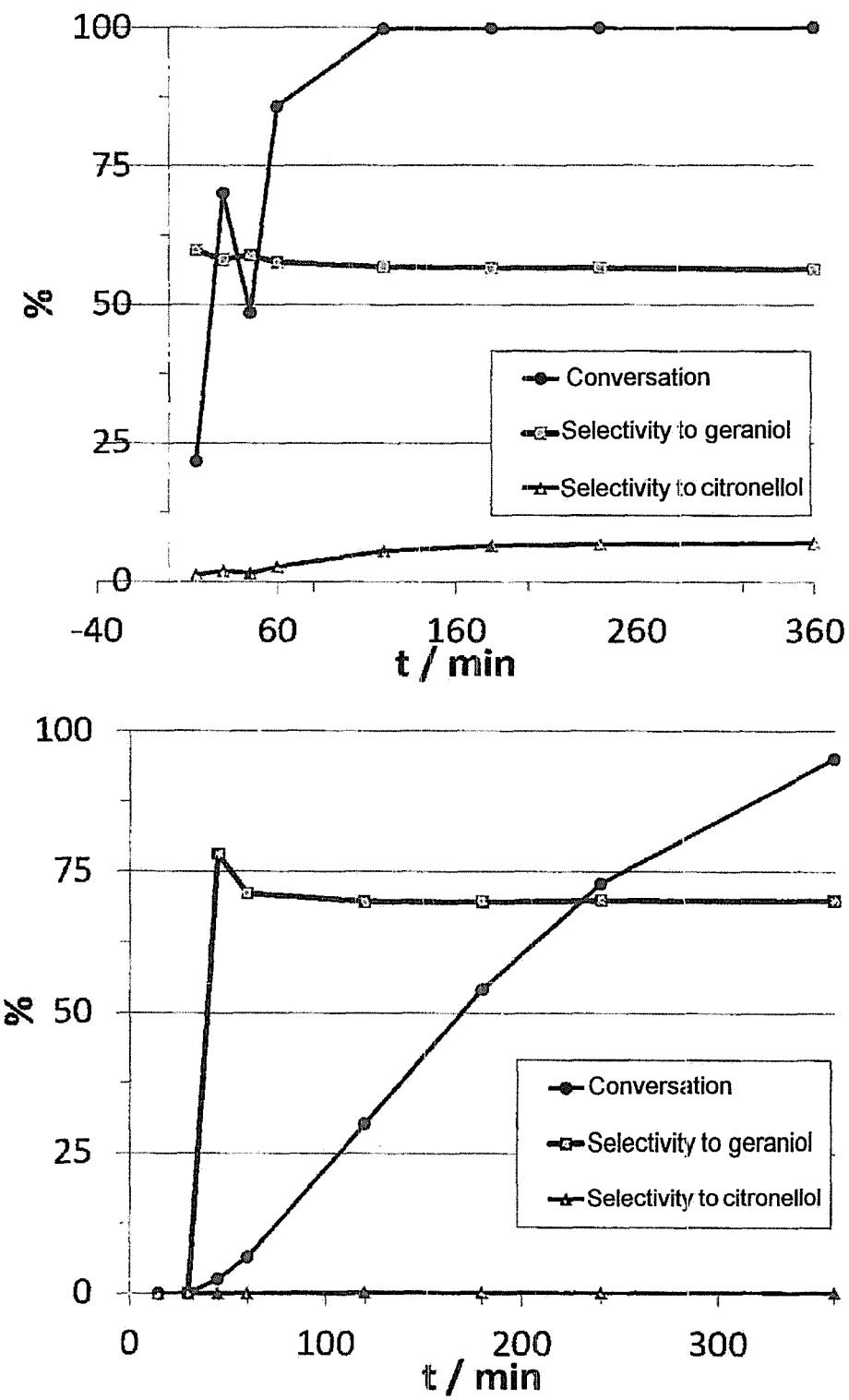

When using the catalyst reduced at 500° C., no complete conversion was achieved in the fourth cycle after 360 minutes (FIG. 2, bottom). In the first cycle, complete conversion was achieved only after 120 minutes (FIG. 2, top).

The invention will now be illustrated with reference to the following nonlimiting examples.

EXAMPLES

Example 1 (Analogous to Examples 1A to 1C of EP 1 317 959)

A) 100 g of activated carbon were admixed with 500 ml of concentrated $HNO_3$ and stirred at 80° C. for 6 hours in a 1 liter flask. After cooling, the mixture was filtered and the filter cake was washed with 10 liters of distilled water.

The moist carbon was returned to the stirred vessel, suspended in 2.5 liters of water and heated to 80° C. under reflux. A solution of 13.11 g of ruthenium chloride and 5.15 g of iron chloride in 375 ml of water was then added dropwise over a period of 120 minutes while stirring. After addition of the metal salt solution, the pH of the suspension was 1.4. The pH was then increased to 9 by slow dropwise addition of 1 M sodium hydroxide solution; about 400 ml of NaOH were consumed here. The mixture was subsequently stirred for another 1 hour and then cooled. The catalyst was transferred to a glass suction filter, washed with a total of 40 liters of water and dried at 80° C. for 6 hours in a vacuum drying oven. The dried powder was then reduced in a stream of 70% of $H_2$ and 30% of $N_2$ at 200° C. in a rotary bulb oven for 3 hours. After the reduction was complete, the powder was cooled under nitrogen and passivated by means of a gas mixture composed of 1% of oxygen in nitrogen. The finished catalyst had a chloride content of less than 0.05% by weight. Furthermore, the following contents (% by weight) were determined: Na: 2.8, Ru: 5.2, Fe: 1.1.

B) The procedure as described in A was repeated, using ruthenium nitrosyl nitrate and iron(III) nitrate instead of ruthenium chloride and iron chloride. The finished catalyst had a ruthenium content of 5.1% by weight, an iron content of 1.1% by weight, a nitrate content of <0.01% by weight and an Na content of 2.1% by weight.

C) The procedure as described in A was repeated, but lower ruthenium and iron contents were applied to the activated carbon. The finished catalyst had a ruthenium content of 2.8% by weight, an iron content of 0.54% by weight, a chloride content of 0.02% by weight and an Na content of 3.8% by weight.

D) 110 g of the activated carbon Norit SX Plus® were, without further pretreatment, introduced into a stirred flask with 2 liters of water, suspended and heated to 80° C. under reflux. The pH was then increased to 9 by addition of aqueous NaOH (1 mol/l). 300 ml of a solution of ruthenium nitrosyl nitrate and iron nitrate (concentralion corresponding to 5.85 g of Ru and 1.17 g of Fe) was then added dropwise at 80° C. over a period of one hour, with the pH being kept at about 9 at the same time by simultaneous addition of aqueous NaOH. The mixture was stirred at 80° C. for another one hour and then cooled. The cold suspension was filtered and the solid was washed with 40 liters of water, then dried at 80° C. for 16 hours in a vacuum drying oven and reduced and passivated as described under A. The catalyst had an Ru content of 5.0% by weight, an Fe content of 1.0% by weight and an Na content of 0.036% by weight.

Example 2 (Analogous to Example 2 of EP 1 317 959)

62 g of activated carbon extrudates (Supersorbon SX 30 from Lurgi, diameter 3 mm, surface area about 1000 m$^2$/g) were placed together with 400 ml of deionized water in a stirred vessel and heated to 80° C. with gentle stirring and under reflux. A solution of 8.13 g of ruthenium chloride and 3.19 g of iron chloride was added dropwise at 80° C. over a period of 60 minutes. The pH was then increased to 9 by addition of 1 M sodium hydroxide solution and the mixture was stirred for another one hour. The catalyst was transferred to a glass suction filter, washed with 10 liters of deionized water and subsequently dried at 80° C. for 6 hours in a vacuum drying oven. The catalyst was then reduced in a gas mixture of hydrogen and nitrogen (4/50) at 200° C. for 3 hours in a reduction oven, cooled to room temperature and passivated by means of a gas mixture composed of 1% of oxygen in nitrogen.

Example 3 (Analogous to Example 1D of EP 1 317 959)

50 g of Norit carbon SX plus were stirred up in 300 ml of distilled water and heated to 80° C. Iron nitrate and ruthenium nitrosyl nitrate in water were then introduced at a pH of 9.0 (maintained by addition of NaOH, 1.5 molar) over a period of about 70 minutes. After stirring for another 1 hour, the carbon was filtered off and washed with about 16 l of water. The catalyst was then dried at 100° C. for 10 hours in a vacuum drying oven. The reduction was carried out in a rotary tube oven into which the catalyst was firstly introduced, after which the oven was heated to 180° C. in a stream of N$_2$, maintained at 180° C. in the stream of N$_2$ (35 standard l/h) for 2 hours then heated under 30 standard l/h of N$_2$ and 4 standard l/h of H$_2$ to 200° C. and maintained at this temperature for 2 hours and cooled, likewise under 30/4 standard l/h of N$_2$/H$_2$. Passivation was carried out in the same apparatus at room temperature. A stream of pure N$_2$ (30 standard l/h) was firstly passed over the catalyst, and, taking account of the temperature, this stream was slowly reduced to 0, while in parallel to this air was slowly fed in until at the end 10 standard l/h of air were fed in at room temperature for 60 minutes. The catalyst was then removed from the reduction reactor in water.

Example 4

The procedure of example 3 was repeated, but passivation was not carried out after the reduction at 200° C., but the catalyst was instead introduced directly into water. The resulting catalyst displayed equally good properties compared to that of example 3.

Comparative Example 1 (Catalyst According to Example 2 of EP 1 317 959)

A catalyst was produced as described in example 2, but the reduction was carried out at 500° C.

Comparative Example 2 (Catalyst According to Example 1D of EP 1 317 959)

The procedure of example 3 was repeated, except that the reduction was carried out according to the prior art at 500° C., i.e. the catalyst was heated to 180° C. in a stream of nitrogen, held for 2 hours (35 standard l/h), then heated under 30 standard l/h of N$_2$ and 4 standard l/h of H$_2$ to 500° C. and held for 2 hours and cooled (likewise under 30/4 standard l/h of N$_2$/H$_2$).

Testing

To compare the catalysts, the reaction of citral was in each case carried out using a catalyst as per example 3 or comparative example 2 according to the following method:

About 3 g of water-moist catalyst according to the invention (FIG. 1—reduction at 200° C.) or according to the prior art (FIG. 2—reduction at 500° C.) (corresponds to about 1.5 g of dry catalyst) were placed in a pressure-rated autoclave (300 ml volume). 105 ml of citral-N and a mixture of 37.4 ml of methanol and 7.5 ml of trimethylamine were in each case added thereto. The autoclave was closed, made inert and pressurized with 30 bar of H$_2$ and heated to 80° C. with the stirrer rotating. During the first hour, a sample was taken via a frit every 15 minutes, and thereafter every hour. After about 6 hours, the experiment was stopped, and the autoclave was depressurized, cooled, and flushed with nitrogen before opening. The samples were analyzed in a gas chromatograph.

Result:

The catalyst which had been reduced at 200° C. according to the present invention is active enough to achieve complete conversion even in the fourth cycle after 360 minutes. In the first cycle, complete conversion was already achieved after 100 minutes.

In comparison, no complete conversion could be achieved in the fourth cycle after 360 minutes when using the catalyst of the comparative example (i.e. according to EP 1 317 959). Even in the first cycle, complete conversion was achieved only after 120 minutes.

The formation of by-products is approximately the same for both catalysts. The selectivity rose during the experiments: in the fourth cycle, neither citronellol nor citronellal is formed.

In summary, it can be said that the catalyst according to the present invention displayed higher stability and activity than the catalyst according to EP 1 317 959 with otherwise equally good properties.

The invention claimed is:

1. A process for producing a ruthenium-iron-carbon support catalyst comprising from 0.1 to 5% by weight of iron in addition to from 0.1 to 10% by weight of ruthenium on a carbon support by
   a) introducing a support into water
   b) simultaneously adding the catalytically active components ruthenium and iron in the form of solutions of their metal salts
   c) coprecipitating the catalytically active components on the support by addition of a base
   d) separating the catalyst from the aqueous phase of the support suspension
   e) drying the catalyst
   f) reducing the catalyst in a stream of hydrogen at from 100 to less than 400° C. in a reduction reactor
   g) removing the catalyst from the reduction reactor under liquids having a flashpoint of greater than 80° C.
   or
   passivating the catalyst by passing a diluted oxygen stream over it
   or
   passivating the catalyst by passing a diluted oxygen stream over it and removal of the catalyst from the reduction reactor under liquids having a flashpoint of greater than 80° C.

2. The process according to claim 1, wherein the catalyst produced is a suspended catalyst.

3. The process according to claim 1, wherein the catalyst produced is a fixed-bed catalyst.

4. The process according to claim 1, wherein steps (b) and (c) are carried out at a temperature of from 50 to 95° C.

5. The process according to claim 1, wherein steps (b) and (c) are carried out either simultaneously or successively.

6. The process according to claim 1, wherein the catalytically active components are used in the form of their chlorides, nitrates, nitrosyl nitrates, acetates, oxides, hydroxides or acetylacetonates.

7. The process according to claim 1, wherein the carbon support is pretreated by oxidation by means of $HNO_3$, oxygen, hydrogen peroxide or hydrochloric acid.

8. The process according to claim 1, wherein $Na_2CO_3$, $NaHCO_3$, $(NH_4)_2CO_3$, $NH_3$, urea, NaOH, KOH or LiOH is used as base for precipitation of the catalytically active components onto the support.

9. The process according to claim 1, wherein NaOH is used for precipitation of the catalytically active components.

10. A process comprising selective liquid-phase hydrogenating carbonyl compounds of the general formula I

where
$R^1$, $R^2$ are, independently of one another, identical or different and are each hydrogen or a saturated or a monounsaturated or polyunsaturated straight-chain or branched, optionally substituted, $C_1$-$C_{20}$-alkyl radical, an optionally substituted aryl radical or an optionally substituted heterocyclic group,
to the corresponding alcohols of the general formula II

where $R^1$, $R^2$ are as defined above;
where the hydrogenation occurs over a catalyst produced by the process according to claim 1.

11. The process according to claim 10, wherein the carbonyl compound is an alpha,beta-unsaturated carbonyl compound.

12. The process according to claim 10, wherein the carbonyl compound is citral.

13. The process according to claim 10, wherein the carbonyl compound is citronellal.

14. The process according to claim 10 as suspended catalyst or fixed-bed catalyst.

15. The process according to claim 1, wherein the reduction in step f) is carried out at from 120 to 300° C.

16. The process according to claim 1, wherein the reduction in step f) is carried out at from 150 to 250° C.

17. The process according to claim 1, wherein the reduction in step f) is carried out at from 180 to 220° C.

* * * * *